(12) United States Patent
Elvira et al.

(10) Patent No.: US 11,452,322 B2
(45) Date of Patent: Sep. 27, 2022

(54) TRAUMATIC BRAIN INJURY PROTECTION DEVICES

(71) Applicant: Q30 SPORTS SCIENCE, LLC, Westport, CT (US)

(72) Inventors: George Elvira, Montreal (CA); Stephan Georgiev, Montreal (CA); Martin Tremblay, Montreal (CA)

(73) Assignee: Q Sports Science, LLC, Westport, CT (US)

( * ) Notice: Subject to any disclaimer, the term of this patent is extended or adjusted under 35 U.S.C. 154(b) by 245 days.

(21) Appl. No.: 15/977,830

(22) Filed: May 11, 2018

(65) Prior Publication Data

US 2018/0325194 A1 Nov. 15, 2018

Related U.S. Application Data

(63) Continuation of application No. PCT/US2016/062335, filed on Nov. 16, 2016.

(Continued)

(51) Int. Cl.

| *A61B 17/132* | (2006.01) |
| *A61B 17/135* | (2006.01) |
| *A41D 27/16* | (2006.01) |
| *F41H 1/00* | (2006.01) |
| *A41D 13/05* | (2006.01) |
| *A61B 5/03* | (2006.01) |

(Continued)

(52) U.S. Cl.
CPC ........... *A41D 27/16* (2013.01); *A41D 13/055* (2013.01); *A61B 5/031* (2013.01); *A61B 17/1325* (2013.01); *A61B 17/1355* (2013.01); *A61F 5/32* (2013.01); *A61F 13/128* (2013.01); *F41H 1/00* (2013.01); *A41D 13/018* (2013.01); *A41D 13/0512* (2013.01); *A41D 2600/10* (2013.01); *A61B 17/135* (2013.01); *A61B 2017/00022* (2013.01); *A61B 2017/00221* (2013.01); *A61B 2090/067* (2016.02); *A63B 71/081* (2013.01); *A63B 71/1291* (2013.01)

(58) Field of Classification Search
None
See application file for complete search history.

(56) References Cited

U.S. PATENT DOCUMENTS

| 428,926 A | 5/1890 | Martin |
| 519,894 A | 5/1894 | Schutz |

(Continued)

FOREIGN PATENT DOCUMENTS

| CA | 2823184 | 9/2015 |
| CA | 3005557 | 5/2017 |

(Continued)

OTHER PUBLICATIONS

EP, 16867063.6 Supplementary Search Report, dated Jun. 18, 2019.

(Continued)

*Primary Examiner* — Shaun L David
(74) *Attorney, Agent, or Firm* — Ruggiero, McAllister & McMahon LLC

(57) ABSTRACT

The disclosure provides neck collar devices and systems for the mitigation and prevention of traumatic brain injury, including concussion. Specifically disclosed are adjustable collars and systems, and collars having certain pressure sensing devices.

22 Claims, 18 Drawing Sheets

Related U.S. Application Data

(60) Provisional application No. 62/256,093, filed on Nov. 16, 2015.

(51) Int. Cl.
  *A61F 5/32* (2006.01)
  *A61F 13/12* (2006.01)
  *A63B 71/12* (2006.01)
  *A61B 17/00* (2006.01)
  *A63B 71/08* (2006.01)
  *A61B 90/00* (2016.01)
  *A41D 13/018* (2006.01)

(56) References Cited

U.S. PATENT DOCUMENTS

| | | |
|---|---|---|
| 1,123,873 A | 1/1915 | Heflin |
| 1,280,742 A | 10/1918 | Hurd |
| 1,473,041 A | 11/1923 | Henderson |
| 1,481,354 A | 1/1924 | Dingfeld |
| 1,592,496 A | 7/1926 | Madden |
| 1,691,856 A | 11/1928 | Robbins |
| 2,091,276 A | 8/1937 | Evangeline, I |
| 2,234,921 A | 3/1941 | Webb |
| 2,271,927 A | 2/1942 | Saighman |
| 2,284,205 A | 5/1942 | Hansen |
| 2,385,638 A | 9/1945 | Norwood |
| 2,676,586 A | 4/1954 | Coakwell, Jr. |
| 2,715,994 A | 8/1955 | Steinacker |
| 3,008,464 A | 11/1961 | Atkins |
| 3,078,844 A | 2/1963 | Scholz |
| 3,171,409 A | 3/1965 | Cetrone |
| 3,477,425 A | 11/1969 | Grassl |
| 3,490,448 A | 1/1970 | Grubb |
| 3,497,872 A | 3/1970 | Mitchell |
| 3,500,472 A | 3/1970 | Castellani |
| 3,595,225 A | 7/1971 | Beeman |
| 3,628,536 A | 12/1971 | Glesne |
| 3,657,739 A | 4/1972 | Holmes, Sr. |
| 3,765,412 A | 10/1973 | Ommaya et al. |
| 3,832,105 A | 8/1974 | Takahashi |
| 3,850,164 A | 11/1974 | Hare |
| 3,901,230 A | 8/1975 | Henkin |
| 4,121,582 A | 10/1978 | Masso Remiro |
| 4,159,020 A | 6/1979 | von Soiron et al. |
| 4,188,946 A | 2/1980 | Watson et al. |
| 4,204,547 A | 5/1980 | Allocca |
| 4,243,028 A | 1/1981 | Puyana |
| 4,272,011 A | 6/1981 | Nagatomo et al. |
| 4,308,861 A | 1/1982 | Kelly |
| 4,336,807 A | 6/1982 | Benckhuijsen |
| 4,343,303 A | 8/1982 | Williams |
| 4,377,159 A | 3/1983 | Hansen |
| 4,479,495 A | 10/1984 | Isaacson |
| 4,549,998 A | 10/1985 | Porter et al. |
| 4,576,150 A | 3/1986 | Auracher |
| 4,628,926 A | 12/1986 | Duncan et al. |
| 4,646,728 A | 3/1987 | Takeda |
| 4,716,898 A | 1/1988 | Chauve et al. |
| 4,817,595 A | 4/1989 | Maass |
| 4,991,576 A | 2/1991 | Henkin et al. |
| 4,997,438 A | 3/1991 | Nipper |
| 5,078,728 A | 1/1992 | Giarratano |
| 5,152,302 A | 10/1992 | Fareed |
| 5,234,459 A | 8/1993 | Lee |
| 5,255,675 A | 10/1993 | Kolobow |
| 5,295,949 A | 3/1994 | Hathaway |
| 5,295,996 A | 3/1994 | Blair |
| 5,302,806 A | 4/1994 | Simmons et al. |
| 5,312,350 A | 5/1994 | Jacobs |
| 5,320,093 A | 6/1994 | Raemer |
| 5,338,290 A | 8/1994 | Aboud |
| 5,375,261 A | 12/1994 | Lipke |
| 5,381,558 A | 1/1995 | Lo |
| 5,398,675 A | 3/1995 | Henkin et al. |
| 5,403,266 A | 4/1995 | Bragg et al. |
| 5,413,582 A | 5/1995 | Eaton |
| 5,497,767 A | 3/1996 | Olsson et al. |
| 5,501,697 A | 3/1996 | Fisher |
| 5,507,280 A | 4/1996 | Henkin et al. |
| 5,507,721 A | 4/1996 | Shippert |
| D369,660 S | 5/1996 | Myoga |
| 5,584,853 A | 12/1996 | McEwen |
| 5,601,598 A | 2/1997 | Fisher |
| 5,643,315 A | 7/1997 | Daneshvar |
| 5,695,520 A | 12/1997 | Bruckner et al. |
| 5,709,647 A | 1/1998 | Ferber |
| 5,776,123 A | 7/1998 | Goerg et al. |
| 5,792,176 A | 8/1998 | Chang |
| 5,806,093 A | 9/1998 | Summers |
| 5,817,218 A | 10/1998 | Hayashi et al. |
| 5,848,981 A | 12/1998 | Herbranson |
| 5,940,888 A | 8/1999 | Sher |
| 5,957,128 A | 9/1999 | Hecker et al. |
| 5,978,965 A | 11/1999 | Summers |
| 6,007,503 A | 12/1999 | Berger et al. |
| D419,267 S | 1/2000 | Hartunian |
| 6,038,701 A | 3/2000 | Regan |
| 6,058,517 A | 5/2000 | Hartunian |
| 6,158,434 A | 12/2000 | Lugtigheid et al. |
| 6,165,105 A | 12/2000 | Boutellier et al. |
| 6,217,601 B1 | 4/2001 | Chao |
| 6,227,196 B1 | 5/2001 | Jaffe et al. |
| 6,238,413 B1 | 5/2001 | Wexler |
| 6,245,024 B1 | 6/2001 | Montagnino et al. |
| 6,274,786 B1 | 8/2001 | Heller |
| 6,344,021 B1 | 2/2002 | Juster et al. |
| 6,354,292 B1 | 3/2002 | Fisher |
| 6,398,749 B1 | 6/2002 | Slautterback |
| 6,423,020 B1 | 7/2002 | Koledin |
| 6,554,787 B1 | 4/2003 | Griffin et al. |
| D475,139 S | 5/2003 | Myoga |
| 6,558,407 B1 | 5/2003 | Ivanko et al. |
| 6,612,308 B2 | 9/2003 | Fisher et al. |
| 6,622,725 B1 | 9/2003 | Fisher et al. |
| 6,623,835 B2 | 9/2003 | Chang |
| 6,655,382 B1 | 12/2003 | Kolobow |
| 6,659,689 B1 | 12/2003 | Courtney et al. |
| 6,663,653 B2 | 12/2003 | Akerfeldt |
| 6,700,031 B1 | 3/2004 | Hahn |
| 6,711,750 B1 | 3/2004 | Yoo |
| 6,766,570 B1 | 7/2004 | Klemm et al. |
| 6,799,470 B2 | 10/2004 | Harada |
| 6,799,570 B2 | 10/2004 | Fisher et al. |
| 6,854,134 B2 | 2/2005 | Cleveland |
| 7,069,598 B1 | 7/2006 | Welch |
| 7,100,251 B2 | 9/2006 | Howell |
| 7,100,606 B2 | 9/2006 | Fisher et al. |
| 7,141,031 B2 | 11/2006 | Garth et al. |
| D539,425 S | 3/2007 | Harrison |
| 7,207,953 B1 | 4/2007 | Goicaj |
| D555,836 S | 11/2007 | Foust et al. |
| 7,452,339 B2 | 11/2008 | Mattison |
| 7,618,386 B2 | 11/2009 | Nordt, III et al. |
| 7,653,948 B2 | 2/2010 | Schwenner |
| 7,981,135 B2 | 7/2011 | Thorpe |
| D653,018 S | 1/2012 | Webbe et al. |
| 8,109,963 B1 | 2/2012 | Korrol |
| 8,376,975 B1 | 2/2013 | Harris, Jr. |
| 8,381,362 B2 | 2/2013 | Hammerslag et al. |
| 8,900,169 B2 | 12/2014 | Smith et al. |
| 8,955,165 B1 | 2/2015 | Romero |
| 8,985,120 B2 | 3/2015 | Smith |
| 9,168,045 B2 | 10/2015 | Smith et al. |
| 9,173,660 B2 | 11/2015 | Smith et al. |
| D763,518 S | 8/2016 | Fletcher et al. |
| 9,913,501 B1 | 3/2018 | Flug |
| 10,905,180 B1 | 2/2021 | Minaev et al. |
| 2002/0004948 A1 | 1/2002 | Son |
| 2003/0130690 A1 | 7/2003 | Porrata et al. |
| 2003/0221554 A1 | 12/2003 | TeGrotenhuis et al. |
| 2004/0127937 A1 | 7/2004 | Newton |
| 2004/0128744 A1 | 7/2004 | Cleveland |
| 2004/0243044 A1 | 12/2004 | Penegor et al. |

(56) References Cited

U.S. PATENT DOCUMENTS

| | | |
|---|---|---|
| 2004/0267178 A1 | 12/2004 | Benckendorff |
| 2005/0131322 A1 | 6/2005 | Harris, Jr. et al. |
| 2005/0262618 A1 | 12/2005 | Musal |
| 2006/0015048 A1 | 1/2006 | Pillai |
| 2006/0122550 A1 | 1/2006 | Weaver |
| 2006/0048293 A1 | 3/2006 | Lewis et al. |
| 2006/0095072 A1 | 5/2006 | TenBrink |
| 2006/0108215 A1 | 5/2006 | Tzedakis et al. |
| 2006/0142675 A1 | 6/2006 | Sargent |
| 2006/0200195 A1 | 9/2006 | Yang |
| 2007/0033696 A1 | 2/2007 | Sellier |
| 2007/0060949 A1 | 3/2007 | Curry |
| 2007/0123796 A1 | 5/2007 | Lenhardt et al. |
| 2007/0260167 A1 | 11/2007 | Heart |
| 2007/0287806 A1 | 12/2007 | Ong et al. |
| 2008/0021498 A1 | 1/2008 | Di Lustro |
| 2008/0038115 A1 | 2/2008 | Burns et al. |
| 2008/0071202 A1 | 3/2008 | Nardi et al. |
| 2008/0132820 A1 | 6/2008 | Buckman et al. |
| 2008/0154140 A1 | 6/2008 | Chang et al. |
| 2008/0200853 A1 | 8/2008 | Tielve |
| 2008/0267843 A1 | 10/2008 | Burns et al. |
| 2008/0319473 A1 | 12/2008 | Rosenbaum |
| 2009/0076421 A1 | 3/2009 | Grant, Jr. |
| 2009/0099496 A1 | 4/2009 | Heegaard et al. |
| 2009/0105625 A1 | 4/2009 | Kohner et al. |
| 2009/0131973 A1 | 5/2009 | Zacharias |
| 2009/0143706 A1 | 6/2009 | Acosta |
| 2009/0173340 A1 | 7/2009 | Lee |
| 2009/0192423 A1 | 7/2009 | Halmos |
| 2009/0209925 A1 | 8/2009 | Marinello et al. |
| 2009/0234261 A1 | 9/2009 | Singh |
| 2009/0299242 A1 | 12/2009 | Hasegawa |
| 2010/0000548 A1 | 1/2010 | Haworth et al. |
| 2010/0042138 A1 | 2/2010 | Duelo Riu |
| 2010/0071169 A1 | 3/2010 | Williams et al. |
| 2010/0088808 A1 | 4/2010 | Rietdyk et al. |
| 2010/0122404 A1 | 5/2010 | Bowlus et al. |
| 2010/0137768 A1 | 6/2010 | Thorgilsdottir et al. |
| 2010/0152771 A1 | 6/2010 | Di Lustro |
| 2010/0179586 A1 | 7/2010 | Ward et al. |
| 2010/0204628 A1 | 8/2010 | Ghajar |
| 2010/0294284 A1 | 11/2010 | Hohenhorst et al. |
| 2010/0318114 A1 | 12/2010 | Pranevicius et al. |
| 2011/0010829 A1 | 1/2011 | Norman |
| 2011/0026934 A1 | 2/2011 | Boyd |
| 2011/0028934 A1 | 2/2011 | Buckman et al. |
| 2011/0040265 A1 | 2/2011 | Lu et al. |
| 2011/0065637 A1 | 3/2011 | Smith |
| 2011/0093003 A1 | 4/2011 | Lee |
| 2011/0107492 A1 | 5/2011 | Hinchey et al. |
| 2011/0257571 A1 | 10/2011 | Fritsch et al. |
| 2011/0270299 A1 | 11/2011 | Rose et al. |
| 2011/0295174 A1 | 12/2011 | Richards |
| 2012/0078157 A1 | 3/2012 | Ravikumar et al. |
| 2012/0197290 A1* | 8/2012 | Smith ............... A41D 13/0512 606/201 |
| 2012/0246974 A1 | 10/2012 | Hammerslag et al. |
| 2012/0291189 A1 | 11/2012 | Chambers et al. |
| 2013/0041303 A1 | 2/2013 | Hopman et al. |
| 2013/0055492 A1 | 3/2013 | Husain |
| 2013/0085426 A1 | 4/2013 | Brodsky |
| 2013/0133648 A1 | 5/2013 | Beach et al. |
| 2013/0146066 A1 | 6/2013 | Croll |
| 2013/0167846 A1 | 7/2013 | Hurley |
| 2013/0239310 A1 | 9/2013 | Flug |
| 2013/0274638 A1 | 10/2013 | Jennings et al. |
| 2013/0304111 A1 | 11/2013 | Zhadkevich |
| 2013/0333708 A1 | 12/2013 | Hassan |
| 2014/0031781 A1 | 1/2014 | Razon-Domingo |
| 2014/0031787 A1 | 1/2014 | Burnes et al. |
| 2014/0142616 A1 | 5/2014 | Smith |
| 2014/0166024 A1 | 6/2014 | Davidson et al. |
| 2014/0236221 A1 | 8/2014 | Zhadkevich |
| 2014/0257155 A1 | 9/2014 | Altinok et al. |
| 2014/0276278 A1 | 9/2014 | Smith et al. |
| 2014/0277101 A1 | 9/2014 | Smith et al. |
| 2014/0343599 A1 | 11/2014 | Smith et al. |
| 2015/0190599 A1 | 7/2015 | Colman et al. |
| 2015/0305751 A1 | 10/2015 | Hoff et al. |
| 2015/0313607 A1 | 11/2015 | Zhadkevich |
| 2016/0044981 A1 | 2/2016 | Frank et al. |
| 2016/0045203 A1 | 2/2016 | Pollock |
| 2016/0169630 A1 | 6/2016 | Augustine et al. |
| 2016/0213381 A1 | 7/2016 | Zhadkevich |
| 2016/0317160 A1 | 11/2016 | Smith et al. |
| 2017/0215769 A1 | 8/2017 | Lu et al. |
| 2017/0215795 A1 | 8/2017 | Ahmad et al. |
| 2018/0085247 A1 | 3/2018 | Trainor et al. |
| 2018/0263841 A1 | 9/2018 | Satake |
| 2018/0325194 A1 | 11/2018 | Elvira et al. |
| 2018/0333159 A1 | 11/2018 | Smith |
| 2020/0266207 A1 | 8/2020 | Liu |
| 2020/0330323 A1 | 10/2020 | Jolly et al. |
| 2021/0182856 A1 | 6/2021 | Kuchenski et al. |
| 2021/0223580 A1 | 7/2021 | Xu |
| 2021/0254179 A1 | 8/2021 | Xu et al. |

FOREIGN PATENT DOCUMENTS

| | | |
|---|---|---|
| CN | 87103201 | 12/1987 |
| CN | 201189186 | 2/2009 |
| CN | 101690658 | 7/2011 |
| CN | 102326890 | 1/2012 |
| CN | 202618320 U | 12/2012 |
| CN | 103384444 A | 11/2013 |
| CN | 103385555 | 11/2013 |
| DE | 3409335 | 9/1985 |
| EP | 0067622 A1 | 12/1982 |
| EP | 2637927 A1 | 9/2013 |
| EP | 2777411 | 9/2014 |
| FR | 719730 | 2/1932 |
| FR | 2041596 | 1/1971 |
| GB | 291600 | 6/1928 |
| GB | 1282097 | 7/1972 |
| GB | 2024644 | 1/1980 |
| JP | 42002568 B | 10/1963 |
| JP | S4814547 | 4/1973 |
| JP | S4499310 | 9/1975 |
| JP | S5429876 | 3/1979 |
| JP | S559202 | 1/1980 |
| JP | S5511002 | 11/1980 |
| JP | S5438272 | 10/1981 |
| JP | S6266102 | 3/1987 |
| JP | H0207814 | 1/1990 |
| JP | H11247001 | 9/1999 |
| JP | 2003135472 | 5/2003 |
| JP | 3098099 U | 2/2004 |
| JP | 2004337393 | 12/2004 |
| JP | 2004036067 | 5/2005 |
| JP | 2005292006 | 10/2005 |
| JP | 3171026 | 10/2011 |
| WO | 1996020783 | 7/1996 |
| WO | 1998046144 | 10/1998 |
| WO | 2008150966 A1 | 12/2008 |
| WO | 2009152649 | 12/2009 |
| WO | 2010056280 | 5/2010 |
| WO | 2011048518 | 4/2011 |
| WO | WO 2012/054262 A1 | 4/2012 |
| WO | 2012168449 | 12/2012 |
| WO | 2013055409 | 4/2013 |
| WO | WO 2013/055409 A1 | 4/2013 |
| WO | 2014143853 | 9/2014 |
| WO | 2015061663 | 4/2015 |
| WO | 2017172964 | 10/2017 |
| WO | 202008500 | 1/2020 |
| WO | 2020005409 | 1/2020 |
| WO | 2020048518 | 3/2020 |
| WO | 2020051545 | 3/2020 |
| WO | 2020054262 | 3/2020 |
| WO | 2020055409 | 3/2020 |
| WO | 2020056280 | 3/2020 |
| WO | 2020061663 | 4/2020 |
| WO | 2020074350 | 4/2020 |

(56) References Cited

FOREIGN PATENT DOCUMENTS

| WO | 2020143853 | 7/2020 |
|----|------------|--------|
| WO | 2020150966 | 7/2020 |
| WO | 2020152649 | 7/2020 |
| WO | 2020156335 | 8/2020 |
| WO | 2020168449 | 8/2020 |
| WO | 2020172964 | 9/2020 |
| WO | 2020200672 | 10/2020 |

OTHER PUBLICATIONS

WO, PCT/US2016/062335 ISR and Written Opinion, dated Jan. 24, 2017.
EP, 16867063.6 Examination Report, dated Jul. 22, 2020.
Vasavada, A. N., et al., "Head and neck anthropometry, vertebral geometry and neck strength in height-matched men and women", Journal of Biomechanics, 2008, vol. 41, pp. 114-121.
Chinese Second Office Action dated Jun. 21, 2021 from corresponding Chinese Patent Application No. 201680066866.X, 12 pages.
Walusinski et al., How Yawning Switches the Default-Mode Network to the Attentional Network by Activating the Cerebrospinal Fluid Flow, Clinical Anatomy 27:201-209 (2014).
Leonard et al., Comparison of central venous and external jugular venous pressures during repair of proximal femoral fracture, British Journal of Anaesthesia (2008), vol. 101, No. 2, pp. 166-170.
Batson, Anatomical Problems Concerned in the Study of Cerebral Blood Flow, Federation Proceedings, Federation of American Societies for Experimental Biology, 1944, 139-144, vols. 3-4.
Cardosoa, Microplate Reader Analysis of Triatomine Saliva Effect on Erythrocyte Aggregation, Antonio Valad, Materials Research, vol. 10, No. 1, 31-362007.
Ferguson, Cervical Collars: A Potential Risk to the Head-Injured Patient, International Journal of Care for the Injured, (1993), vol. 24, No. 7, pp. 454-456.
Finnie, Animal Models Traumatic Brain Injury, Veterinary Pathology, 2002, 679-689, vol. 39.
Fuster, Woodpecker Drilling Behavior, Arch Nero 36370-373.
Gilland, A Cinemyelographic Study of Cerebrofspinal Fluid Dynamics, Amer J of Roent, 106 (2): 369 (1969).
Gregg, Experimental Approaches to the Study of the Cerebral Circulation, Fed. Proc., 1944, 3:144.
Hartlage, Brain Injury from Motor Vehicle Accidents, Preventable Damage: Brain Vulnerability and Brain Health. New York: Springer Publishing Company 1992.
Kitano, The Elasticity of the Cranial Blood Pool, Journal of Nuclear Medicine 5:613-625, 1964.
May, Woodpecker Drilling Behavior, an Endorsement of the Rotational Theory of Impact Brain Injury, Arch Neurology, Jun. 1979, 370-373, vol. 36.
Moyer, Effect of Increased Jugular Pressure on Cerebral Hemodynamic, Journal of Applied Physiology, Nov. 1954, 245-247, vol. 7, No. 3.
Torres, Changes in the electroencephalogram and in systemic blood pressure associated with carotid compression, Neurology 1970; 20:1077-1083.
Tyrell, Observations on the C.S.F Pressure during Compression of the Jugular Veins, Postgrad. Med. J. 1951;27;394-395.
Vannucci, Carbon dioxide protects the perinatal brain from hypoxic-ischemic damage: an experimental study in the immature rat, Department of Pediatrics (Pediatric Neurology), Jun. 1995, 868-874, vol. 95, No. 6.
Performance Sports Group Ltd., "Performance Sports Group and Leading Medical Experts Unveil First-of-its-Kind Technology to Address Mild Traumatic Brain Injury" PR Newswire, Nov. 17, 2015.
Omalu "Concussions and NFL: How the name CTE came about" CNN, Dec. 22, 2015.
Baum "St. X, Moeller aid in concussion prevention study" Cincinnati.com, Jan. 8, 2016.
Orcutt "New Collar Promises to Keep Athletes' Brains from "Sloshing" During Impact" MIT Technology Review, Feb. 3, 2016.
Taylor "New wearable neck collar could help reduce brain injuries in athletes" Sports Illustrated, Jun. 15, 2016.
Templer, Donald I., et al., "Preventable Brain Damage, Brain Vulnerability and Brain Health," Part I: Impact Damage ECT and Permanent Brain Damage, Springer Publishing Company, New York pp. 95-107 (1992).
Brain Injury Association of America Transportation-related incidents are leading cause of brain injury www.biausa.org; Apr. 2001.

\* cited by examiner

TRAUMATIC BRAIN INJURY PROTECTION DEVICES

CROSS-REFERENCE TO RELATED APPLICATIONS

The subject application is a continuation of PCT Patent Application No. PCT/US16/62335, filed Nov. 16, 2016, which claims priority to U.S. Provisional Patent Application No. 62/256,093, filed on Nov. 16, 2015, both of which are incorporated by reference herein in their entirety for all purposes.

FIELD OF THE INVENTION

The present invention provides neck collar devices and systems for the mitigation and prevention of traumatic brain injury, including concussion.

BACKGROUND OF THE INVENTION

Traumatic brain injury (TBI) may occur when a person experiences an impact or external force. For example, TBI may arise is sports in which players make physical contact with each other or the ground/playing surface (e.g., football, ice hockey, etc.) or contact with a ball (e.g., soccer). TBI also may arise when individuals (military personnel) are subject to blast or pressure waves, including those caused by explosive devices. Generally, the injurious force may be applied to the head or elsewhere on the body in a manner that either transfers the force to the head or causes the head to undergo a rapid rotation, acceleration, and/or deceleration.

Helmets are normally used to protect the head against injury. It has been found that helmets can be very effective for protection against penetrating brain injury and skull fractures, but have shown little effect in protecting against intracranial injuries such as concussion. It is believed that these intracranial injuries result from the rotational and other forces experienced by the brain during a collision, blast wave, and/or rapid acceleration/deceleration.

It has been discovered that increasing the intracranial blood pressure and/or volume can reduce or prevent the incidence of TBI in the absence of a penetrating brain injury by increasing the coefficient of restitution of the brain structure itself. (see, for example, U.S. Pat. Nos. 8,985,120, 9,168,045, 9,173,660 and 8,900,169, and U.S. patent application Ser. Nos. 13/489,536 , now U.S. Pat. No. 10,004,515 and 14/317,282, now U.S. Pat. No. 10,842,502.) One safe and effective method for increasing intracranial blood pressure and/or volume is by the partial or total occlusion of blood flow through one or more neck veins (e.g., the internal jugular vein(s) and/or the external jugular vein(s)). Thus, there is a need for convenient, wearable devices that occlude neck vein blood flow and are capable of accurate sizing, positioning, and neck vein pressure delivery.

SUMMARY OF THE INVENTION

The present invention provides modular collars, expandable collars, and systems and components for constructing modular and expandable collars that may be used to reduce the severity of, or prevent the occurrence of a traumatic brain injury (TBI) (e.g., a concussion) in a subject wearing the collar. In some embodiments, the TBI is mitigated or prevented when the subject experiences an external concussive force (e.g., a collision or a blast wave) delivered to any part of the body including, for example, the head. The collar functions by applying pressure to one or more (e.g., 2, 3, 4, or more) neck veins including, for example, the internal jugular vein (IJV), external jugular vein (EJV), or both. Neck vein pressure is applied before and during the external concussive force.

In one aspect, the invention provides a modular collar sized to be worn around the neck of a human subject, the collar comprising: (a) a central member having a first mating pair member at a first end and a second mating pair member at a second end; (b) a first side member having a complimentary first mating pair member at a first end and a first compressor at a second end; and (c) a second side member having a complimentary second mating pair member at a first end and a second compressor at a second end. The collar is assembled by mating the first mating pair member with the complimentary first mating pair member and mating the second mating pair member with the complimentary second mating pair member such that the assembled collar has a substantially circular shape (e.g., circular, oval, or elliptical) defining an arc of greater than 180° (e.g., greater than 210°, 240°, 270°, 300°, or 330°, or any intermediate range thereof including, for example between about 180° and 300°).

In another aspect, the invention provides a modular collar system for constructing a collar sized to be worn around the neck of a human subject, the system comprising: (a) one or more central members having a first mating pair member at a first end and a second mating pair member at a second end; (b) one or more first side members having a complimentary first mating pair member at a first end and a first compressor at a second end; and (c) one or more second side members having a complimentary second mating pair member at a first end and a second compressor at a second end. The system is used to assemble one or more collars, as defined above. Each collar is assembled by selecting a central member, a first side member, and a second side member such that the fully assembled collar has the appropriate size and features desired by the user. The collar is assembled by mating the first mating pair member (on the selected first side arm) with the complimentary first mating pair member (on the selected central member) and mating the second mating pair member (on the selected second side arm) with the complimentary second mating pair member (on the selected central member) such that the assembled collar has a substantially circular shape (e.g., circular, oval, or elliptical) defining an arc of greater than 180° (e.g., greater than 210°, 240°, 270°, 300°, or 330°, or any intermediate range thereof including, for example between about 180° and 300°). Optionally, the system provides two or more (e.g., 2, 3, 4, 5, 6, or more) central members. Optionally, the system provides, instead or in addition to multiple central members, two or more (e.g., 2, 3, 4, 5, 6, or more) first side members and second side members. In one embodiment, the first and second side members are provided in matched pairs and, therefore, are present in equal numbers; although this is not necessarily the case.

In any of the foregoing aspects, the assembled collar generally will be symmetrical (e.g., the first and second side members having the same length, curvature, and other structural/functional features), but asymmetrical collars may be constructed either through the use of differently-sized side members or an offset central member (i.e., that is not symmetrical on either side of its central axis). When assembled, the first and second compressors are positioned on the collar such that they contact two or more neck veins of the subject when the collar is worn around the neck, and the collar is adapted to exert an inwardly-directed force on the first and second compressors when worn. The mating pair members may form a reversible attachment, a permanent/irreversible attachment, or a slidable attachment (whether reversible or irreversible) to form a modular and adjustable collar.

In any of the foregoing aspects, first and second compressors may be permanently affixed to the side members or they may be removable. Optionally, the compressors are slidably engaged with the side members in a manner that allows for translocation along the body-facing surface of the collar. In some embodiments, the compressors are expandable in the body-facing direction (i.e., expansion increases the thickness of the collar body/compressor combination in order to apply more pressure to the neck veins and/or provide a tighter/more secure fit). Optionally, the compressors are inflatable (e.g., contains an inflatable bladder). The inflatable element may be inflated using an integrated pump (e.g., a bulb pump) or may be inflated via a connection to an external gas source. Optionally, the inflatable element also contains a pressure release valve that may be configured to automatically release the inflation gas when a pre-determined pressure is exceeded and/or may be manually operated to release the inflation gas.

In any of the foregoing aspects, the central member(s) also contains a fit adjustment element attached to the body-facing surface. The fit adjustment element may be permanently affixed to the central member or it may be removable. It may comprise a rigid, semi-rigid, and/or compressible form, such as a foam pad or hard plastic shape. Optionally, the fit adjustment element is inflatable (e.g., contains an inflatable bladder). The inflatable element may be inflated using an integrated pump (e.g., a bulb pump) or may be inflated via a connection to an external gas source. Optionally, the inflatable element also contains a pressure release valve that may be configured to automatically release the inflation gas when a pre-determined pressure is exceeded and/or may be manually operated to release the inflation gas.

In another aspect, the invention provides a modular collar system for constructing a collar sized to be worn around the neck of a human subject, the system comprising (a) one or more (e.g., 1, 2, 3, 4, 5, 6, or more) central members having a first mating pair member at a first end and a second mating pair member at a second end; (b) one or more (e.g., 1, 2, 3, 4, 5, 6, or more) first side members having a complimentary first mating pair member at a first end and a third mating pair member at a second end; (c) one or more (e.g., 1, 2, 3, 4, 5, 6, or more) second side members having a complimentary second mating pair member at a first end and a third mating pair member at a second end; (d) one or more (e.g., 1, 2, 3, 4, 5, 6, or more) first compressors and one or more (e.g., 1, 2, 3, 4, 5, 6, or more) second compressors, each having a complimentary third mating pair member on an outward-facing side. The system is used to assemble one or more collars, as defined above. Each collar is assembled by selecting a central member (if more than one is provided), a first side member (if more than one is provided), a second side member (if more than one is provided), a first compressor (if more than one is provided), such that the fully assembled collar has the appropriate size and features desired by the user. The collar is assembled by mating the first mating pair member (on the selected first side arm) with the complimentary first mating pair member (on the selected central member) and mating the second mating pair member (on the selected second side arm) with the complimentary second mating pair member (on the selected central member) such that the assembled collar has a substantially circular shape (e.g., circular, oval, or elliptical) defining an arc of greater than 180° (e.g., greater than 210°, 240°, 270°, 300°, or 330°, or any intermediate range thereof including, for example between about 180° and 300°). Each compressors is attached to its respective side member by mating the third mating pair member on the side member with the corresponding complimentary third mating pair member on the compressor. It is understood that the order of assembly is not important to the overall construction of the device. In some embodiments, the first and second side members are provided in matched pairs and, therefore, are present in equal numbers; although this is not necessarily the case.

The assembled collar generally will be symmetrical (e.g., the first and second side members having the same length, curvature, and other structural/functional features), but asymmetrical collars may be constructed either through the use of differently-sized side members or an offset central member (i.e., that is not symmetrical on either side of its central axis). When assembled, the first and second compressors are positioned on the collar such that they contact two or more neck veins of the subject when the collar is worn around the neck, and the collar is adapted to exert an inwardly-directed force on the first and second compressors when worn. The mating pair members may form a reversible attachment, a permanent/irreversible attachment, or a slidable attachment (whether reversible or irreversible) to form a modular and adjustable collar.

In some embodiments, the first and second compressors are provided in matched pairs and, therefore, are present in equal numbers; although this is not necessarily the case. The mating pair members may form a reversible attachment, a permanent/irreversible attachment. Optionally, the compressors are slidably engaged with the side members in a manner that allows for translocation along the body-facing surface of the collar. In some embodiments, the compressors are expandable in the body-facing direction (i.e., expansion increases the thickness of the collar body/compressor combination in order to apply more pressure to the neck veins and/or provide a tighter/more secure fit). Optionally, the compressors are inflatable (e.g., contains an inflatable bladder). The inflatable element may be inflated using an integrated pump (e.g., a bulb pump) or may be inflated via a connection to an external gas source. Optionally, the inflatable element also contains a pressure release valve that may be configured to automatically release the inflation gas when a pre-determined pressure is exceeded and/or may be manually operated to release the inflation gas.

In some embodiments, the central member(s) also contains a fit adjustment element attached to the body-facing surface. The fit adjustment element may be permanently affixed to the central member or it may be removable. It may comprise a rigid, semi-rigid, and/or compressible form, such as a foam pad or hard plastic shape. Optionally, the fit adjustment element is inflatable (e.g., contains an inflatable bladder). The inflatable element may be inflated using an integrated pump (e.g., a bulb pump) or may be inflated via a connection to an external gas source. Optionally, the inflatable element also contains a pressure release valve that may be configured to automatically release the inflation gas when a pre-determined pressure is exceeded and/or may be manually operated to release the inflation gas.

In another aspect, the invention provides an expandable collar sized to be worn around the neck of a human subject, the collar comprising: (a) a central member having a first end and a second end; (b) a first side member having a first end slidably engaged with the first end of the central member and a second end comprising a first compressor; and (c) a second side member having a first end slidably engaged with the second end of the central member and a second end comprising a second compressor, wherein the collar defines an arc of greater than 180° (e.g., greater than 210°, 240°, 270°, 300°, or 330°, or any intermediate range thereof including, for example between about 180° and 300°) having a diameter D; and wherein diameter D is altered by the slidable engagement of the first side member and central member, and the slidable engagement of the second side member and the central member; and wherein the collar is adapted to exert an inwardly-directed force on the first and second compressors when worn.

The compressors may be removable from the side members or permanently attached and may be slidably engaged or immobilized, as described herein. In some embodiments, the compressors are expandable in the body-facing direction (i.e., expansion increases the thickness of the collar body/compressor combination in order to apply more pressure to the neck veins and/or provide a tighter/more secure fit). Optionally, the compressors are inflatable (e.g., contains an inflatable bladder). The inflatable element may be inflated using an integrated pump (e.g., a bulb pump) or may be inflated via a connection to an external gas source. Optionally, the inflatable element also contains a pressure release valve that may be configured to automatically release the inflation gas when a pre-determined pressure is exceeded and/or may be manually operated to release the inflation gas. In some embodiments, the invention provides a system comprising the expandable collar and a two or more pairs of removable compressors. The compressors are provided in matched pairs and, therefore, are present in equal numbers; although this is not necessarily the case.

In any of the foregoing aspects, the central member(s) also contains a fit adjustment element attached to the body-facing surface. The fit adjustment element may be permanently affixed to the central member or it may be removable. It may comprise a rigid, semi-rigid, and/or compressible form, such as a foam pad or hard plastic shape. Optionally, the fit adjustment element is inflatable (e.g., contains an inflatable bladder). The inflatable element may be inflated using an integrated pump (e.g., a bulb pump) or may be inflated via a connection to an external gas source. Optionally, the inflatable element also contains a pressure release valve that may be configured to automatically release the inflation gas when a pre-determined pressure is exceeded and/or may be manually operated to release the inflation gas.

In another aspect, the invention provides a method for reducing or preventing a TBI, or an injury to the inner ear and/or an ocular structure caused by exposure to a concussive force by applying a collar device, as described herein, to the neck of a subject (e.g., a subject identified as being at risk of exposure to a concussive force) prior to and during exposure to that concussive force.

DETAILED DESCRIPTION OF THE INVENTION

Figure 1:
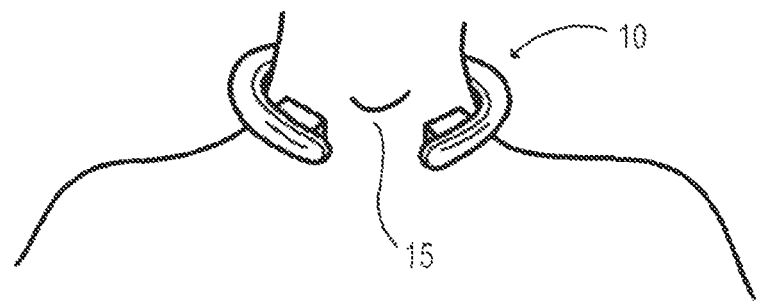
FIG. 1 illustrates a partially-circumferential collar worn around the neck of a subject, wherein the collar is open at the laryngeal prominence.

The present invention provides collar devices that are designed to be worn around the neck of the subject and apply pressure one or more (e.g., two, three, four, or more) neck veins including, for example, the internal jugular veins (IJV) and external jugular veins (EJV). The collars are partially circumferential (i.e., extend around only a portion of the subject's neck). In some embodiments, the partially-circumferential collars are open at the back or at the front (i.e., exposing the laryngeal prominence) and are designed such that the subject's neck passes through the opening when the collar is donned. Optionally, the front of a back-opened collar (i.e., region that overlies the throat and laryngeal prominence) contains a protective rigid member that is useful to protect the underlying neck structures from slashes (e.g., from hockey skates) or blunt trauma caused by contact with another piece of sporting equipment (e.g., puck, ball, stick, racquet, etc.). Likewise, front-opened collars may have a similar protective piece that may be independently affixed after the collar is donned. For example, the rigid front protective member may be entirely removable and attachable using any type of suitable reversible closures, or may be engaged by a hinge on one side and a reversible closure on the other so that the front opening may be open to allow passage of the neck during donning, followed by closure of the front protective member after the collar is in place.

The collars have inwardly-directed compressors which may be protuberances or thickened regions that contact the neck in region overlying the neck veins such that pressure is applied to those neck veins. The inwardly-directed protuberances may be a non-inflatable rigid or semi-rigid stud or pad made of plastic, foam, metal or any other suitable material, or an inflatable member such as a pad. The thickened regions may inflatable or non-inflatable, may be rigid or semi-rigid, and may be formed from any suitable material including plastic, foam, or metal. Any inflatable element has an inflation device which may be an integral or operably-linked bulb pump that is integral to the collar, or a port from inflation from an external pressurized gas source. Optionally, any of the inflatable elements is operably linked to a pressure release valve that may be configured to automatically release/vent the inflation gas upon a predetermined pressure.

Optionally, the collars may contain one or more monitoring or recording devices including, for example, a pressure sensor and accelerometer. Optionally, the collar device has a wired or wireless communication interface operably linked to the sensor(s) and an optional digital memory unit configured for storing sensor data. Communication interfaces may be a radio frequency transmitter (e.g., Bluetooth, WiFi, etc.) or a wired interface (e.g., USB port).

The principles and features of the construction and use of the collars are described herein an in U.S. Pat. Nos. 8,985,120, 9,168,045, and 9,173,660, U.S. Patent Publications 2014/0142616 and 2014/0343599, and PCT publications WO 2012/054262 and WO 2013/05409, each of which is hereby incorporated by reference in its entirety.

Collar Design and Construction

Figure 2:
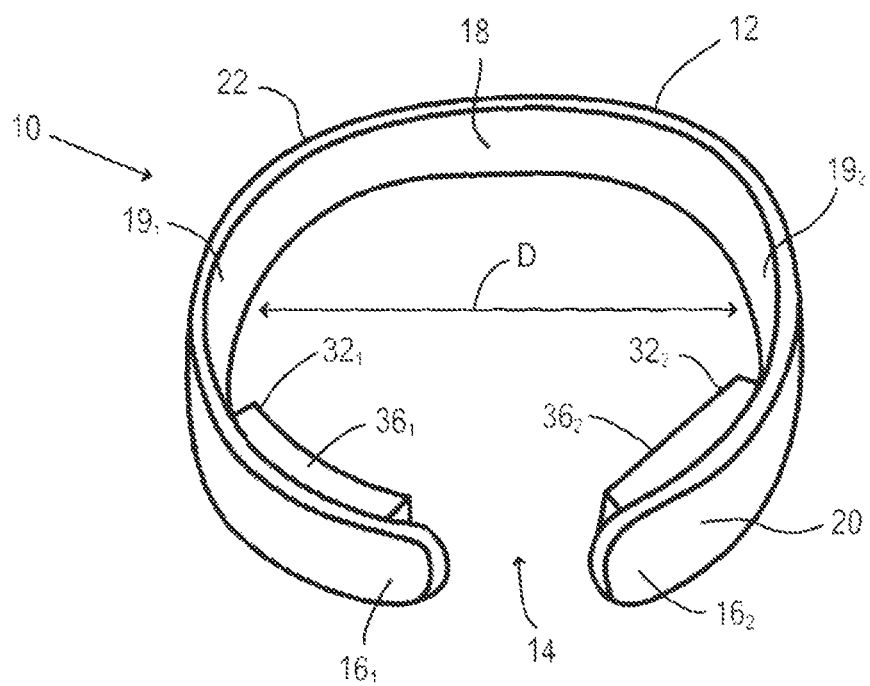
FIG. 2 is a schematic of a unitary collar body illustrating certain features of the collar body and collar device.
Figure 3:
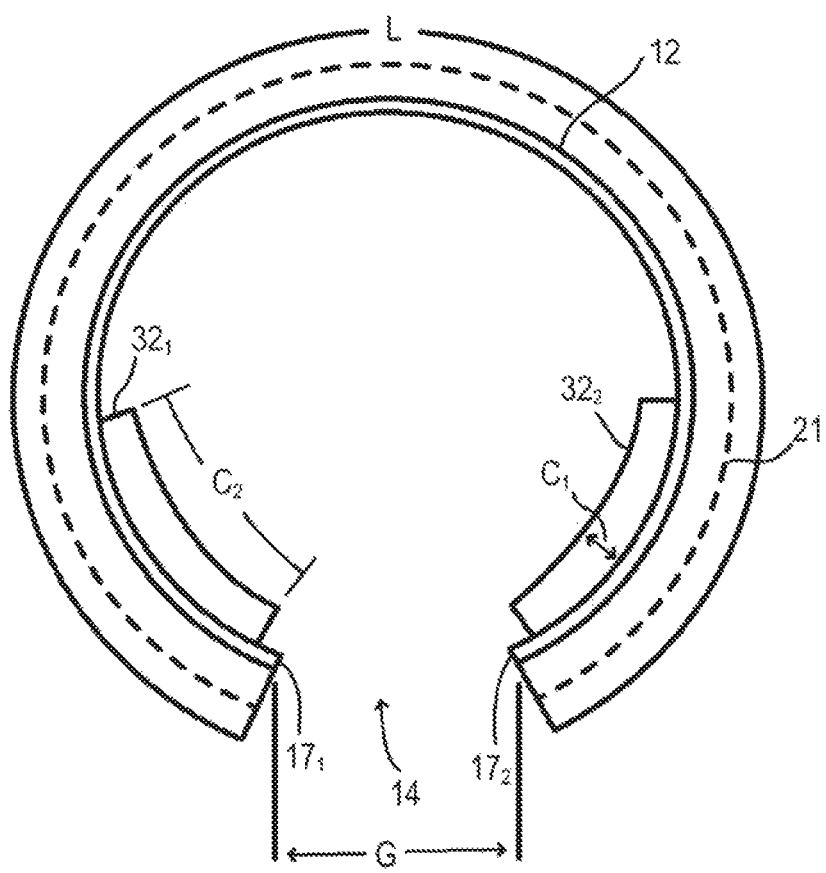
FIG. 3 is a plan view of a unitary collar body.

FIGS. 1-3 show an example of a collar 10 adapted to be worn on a subject's neck to protect the subject against a traumatic brain injury (TBI), such as a concussion, caused by an impact or other external force. The collar 10 is configured to apply pressure on one or more neck veins. The pressure applied to the neck veins may be any pressure that results in an increase in the intracranial blood pressure and/or intracranial blood volume. Suitable pressures include, for example, about 5-100 mm Hg, 5-80 mm Hg, 10-80 mm Hg, 20-60 mm Hg, and 30-50 mm Hg, or at least about 5, 10, 15, 20, 25, 30, 35, 40, 45, 50, 60, 70, 80 mm Hg. Optionally, the collar is configured to limit the maximum neck vein pressure to not more than about 40, 50, 60, 70, 80, 90, or 100 mm Hg.

FIG. 1 illustrates collar 10 worn around the subject's neck. Collar 10 is partially circumferential and open at the front, specifically open to expose the laryngeal prominence 15. In this configuration, collar 10 is stretched such that the subject's neck passes through opening 14 (see, FIG. 2) when donned, and the shape memory property of the collar 10 reduces the opening 14 size such that collar 10 applies pressure the neck vein(s).

FIG. 2 illustrates the features of collar 10 in more detail. Collar 10 comprises body 12 to apply the pressure on the veins of the wearer's neck. In one embodiment, body 12 has a memory shape property having an inwardly-directed bias at end portions 16. Body 12 comprises a neck-engaging inner surface 18 and an outer surface 20 opposite to the inner surface 18. Body 12 has a longitudinal axis 21 (see, FIG. 3) and wraps at least partially about the wearer's neck.

Collar 10 (and body 12) includes an opening 14 that forms a discontinuity or gap in the collar 10 such that it does not extend around the entirety of the circumference of the wearer's neck. This may help for donning the collar 12 and/or comfort. The body 12 includes end portions $16_1$, $16_2$ that define the opening 14. In this example, the opening 14 of the body 12 is located in a front of the wearer's neck when the collar 10 is worn. More particularly, in this embodiment, the opening 14 of the collar 10 is disposed to overlie a laryngeal prominence 15 of the wearer's neck. The opening 14 of the collar 10 may be located elsewhere about the wearer's neck (e.g., on a side or a back of the wearer's neck) in other examples.

For example, in this embodiment, the collar 12 comprises a band 22 configured to deform (i.e., change in shape) when the collar 12 is donned by the wearer and to cause the collar 12 to apply the pressure on the veins of the wearer's neck when the collar 12 is worn on the wearer's neck. For instance, in this case, the band 22 allows the opening 14 of the collar 12 to be enlarged when the collar 12 is donned by moving the end portions $16_1$, $16_2$ of the collar 12 away from one another and then causes the opening 14 of the collar 12 to be reduced by moving the end portions $16_1$, $16_2$ of the collar 12 back towards one another, thereby causing the collar 12 to apply the pressure on the veins of the wearer's neck.

In some embodiments, body 12 comprises band 22 is resilient to change in shape when the collar 10 is donned by the wearer by moving the end portions $16_1$, $16_2$ of the collar 10 away from one another and to bias the end portions $16_1$, $16_2$ of the collar 10 back towards one another for causing the collar 10 to apply the pressure on the veins of the wearer's neck when the collar 10 is worn on the wearer's neck. Band 22 may comprises a C- or U-shaped spring or a resilient arcuate band and may be formed from a polymeric material, a metallic material, a composite material, or any other suitable material that allows the band 22 to resiliently change in shape when the collar 10 is donned by the wearer and to cause the collar 10 to apply the pressure on the veins of the wearer's neck when the collar 12 is worn on the wearer's neck.

Body 12 further comprises a plurality of compressors $32_1$, $32_2$ configured to apply the pressure on the veins of the wearer's neck. The compressors $32_1$, $32_2$ are arranged such that the collar 10 presses more on the wearer's neck where the compressors $32_1$, $32_2$ are located than elsewhere. This allows a pressure applied by the collar 10 on a region of the wearer's neck where the veins are located to be greater than a pressure applied by the collar 10 in another region of the wearer's neck which is engaged by the collar 10 away from the veins (e.g., the back of the wearer's neck). Thus, this may allow the collar 12 to optimally press on the wearer's neck for mitigation against TBI while maintaining comfort.

The compressors $32_1$, $32_2$ may be implemented in any suitable way. For example, in this embodiment, the compressors $32_1$, $32_2$ respectively comprise compressing protuberances $36_1$, $36_2$ that project inwardly towards the wearer's neck when the collar 12 is worn. The compressing protuberances $36_1$, $36_2$ are therefore such that the neck-engaging inner surface 18 of the collar 12 presses more against the wearer's neck where the compressing protuberances $36_1$, $36_2$ are located than elsewhere. In this example, the compressing protuberances $36_1$, $36_2$ are formed by enlargements of the body 12 where it is to press against the veins of the wearer's necks. More particularly, in this example, the enlargements forming the compressing protuberances $36_1$, $36_2$ are made by widening the band 22 where the collar 12 is to press against the veins of the wearer's necks.

The collar 10 may be constructed in any other suitable way in other embodiments to apply the pressure on the veins of the wearer's neck to effectively provide protection against TBI. For example, in some embodiments, body 12 may be inflatable (e.g., the compressors $32_1$, $32_2$ and/or another part of the body 12 may be inflatable by air or another gas, such as by comprising an inflatable bladder and a valve).

It is understood that there is variability between individuals with respect to neck size/diameter. For example, adults generally have a larger neck diameter than children, and men often have a larger neck diameter than women, although there is significant overlap between virtually any demographic groups that one compares, and there is significant inter-individual variability even within demographic groups. Thus, it is desirable to provide collar device that are adjustable. In particular, it is desirable to provide collars and collar systems in which the collar diameter can be varies and/or the relative placement of the compressors can be altered for any given collar diameter.

As described in more detail below, adjustments to the collar 10 and/or body 12 may include:

A length L of the body 12. In this embodiment where the body 12 is a partial collar, the length L of the body 12 is defined between ends $17_1$, $17_2$ of the body 12;

An internal dimension D of the body 12 taken between opposite sides $19_1$, $19_2$ of the neck-engaging inner surface 18 of the body 12;

A dimension G of the opening 14 of the body 12;

Positions of the compressors $32_1$, $32_2$ on the body 12, such as along the longitudinal axis 21 of the body 12;

Dimensions of the compressors $32_1$, $32_2$, such as a dimension $C_1$ (e.g., thickness) of each compressor 32 normal to the longitudinal axis 21 of the body 12 and/or a dimension $C_2$ (e.g., length) of the compressor 32 along the longitudinal axis 21 of the body 12;

An internal pressure of a gas (e.g., air) within the body 12 (e.g., within an inflatable member of the body 12) in embodiments where the body 12 is inflatable; and/or Any other setting of the body 12 that affects the pressure it applies and/or where it applies the pressure on the wearer's neck.

Adjustable Collar Bodies

Figure 4:
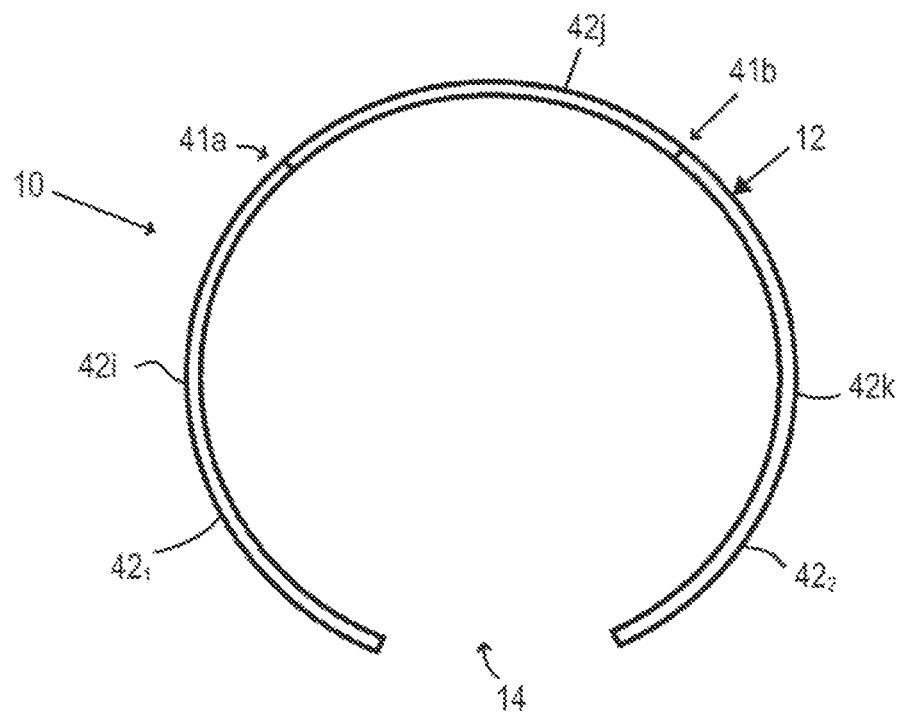
FIG. 4 is a schematic of a modular collar body.
Figure 5:
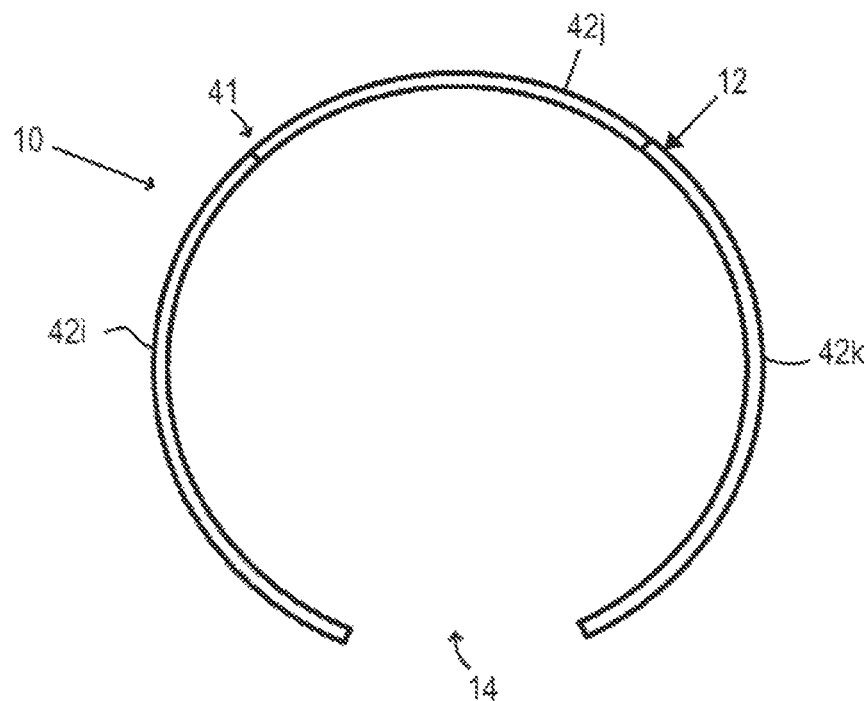
FIG. 5 is a schematic of another modular collar body.
Figure 6:
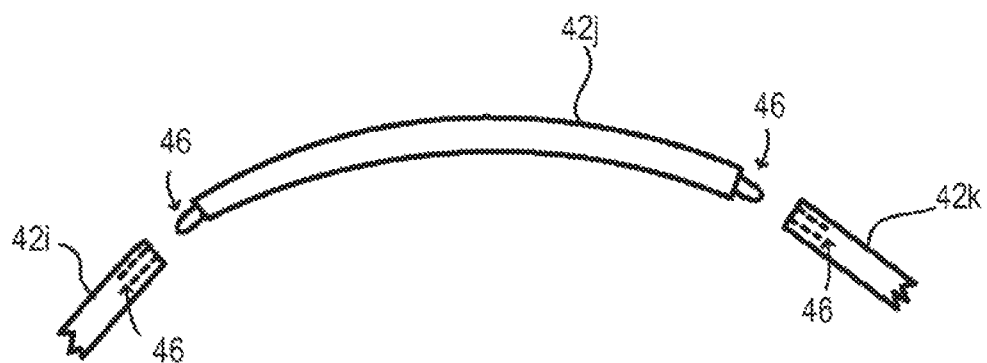
FIG. 6 is a schematic of a connector system that may be used with the various elements of a modular collar body.

FIGS. 4-6 illustrate some embodiments of adjustable collar bodies 12 in which the diameter D and/or length L of the body 12, and therefore the collar 10, may be altered. Specifically, in some embodiments, the invention provides a collar body system having a first side member 42*i*, a second side member 42*k*, and a central member 42*j*. Each of the first side members 42*i* and second side members 42*k* have a compressor 32 located on the inner-facing surface 18 toward or at the end portions $16_1$, $16_2$. Typically, the first side members 42*i* and second side members 42*k* have and equal length but opposite orientation to serve as a left-side member and a right-side member. The collar body 12 is formed by permanently or reversible engaging the first side members 42*i* with a first end of the central member 42*j* at joint 41*a*, and permanently or reversible engaging the second side members 42*k* with a second end of the central member 42*j* at joint 41*b*, such that a complete body 12 is formed with the compressors 32 located on the inner facing surface 18 toward or at the end portions $16_1$, $16_2$. The combination of the first and second side members with the central member form the collar body 12.

The invention also provides collar systems which may contain a plurality of central members 42*j* and/or a plurality of matched pairs of first and second side members 42*i*, 42*k*. In some embodiments, the system contains a single central member 42*j* and a plurality of matched pairs of first and second side members 42*i*, 42*k* (e.g., two, three, four, or more matched pairs). In other embodiments, the system contains a plurality of central members 42*j* with one or more matched pairs of first and second side members 42*i*, 42*k* (e.g., one, two, three, four, or more matched pairs). In system embodiments for which a plurality of matched pairs of first and second side members 42*i*, 42*k* are provided, the various side member pairs may differ from each other in side length (i.e., length from joint 41 to the terminus of the end portion 16 and/or the curvature of the side members. For example, a system may provide three matched side member pairs characterized as having a short, medium, and long length. Alternatively or in addition to variations in side member length, the curvature of side members may be varies among the pairs in order to accommodate differently-shaped necks. For example, one side member pair may be nearly straight with other side member pairs defining a larger arc over the same or different length. In system embodiments for which a plurality of central members 42*j* are provided, the central members may vary from each other in length and/or curvature. Such systems allow the user to customize the fit of the collar device by selecting the central member and/or side member pair that most closely approximates the neck circumference and results in the most accurate placement of the compressors 32 on the target neck veins.

FIGS. 4 and 5 illustrate two embodiments of these collar bodies and systems. FIG. 4 illustrates an assembled modular collar body 12 that uses a relatively long central member 42*j*, resulting in a relatively narrow opening 14 and smaller diameter D. In contrast, FIG. 5 illustrates an assembled modular collar body 12 that uses a relatively short central member 42*j*, resulting in a relatively larger opening 14 and larger diameter D.

Joints 41 may be any suitable reversible or irreversible joining/locking mechanism that securely fastens the side members to the central member and retains the assembled device in a rigid form that maintains the spring-like property of the body that causes an inwardly-directed force on the compressors 32. For example and as shown in FIG. 6, the connector 46 at each end of the central member 42*j* comprises a male pair member (e.g., a projection) and each end of the side members 42*i* and 42*k* comprises a female pair member (e.g., a hollow space such as a recess or an opening) engageable with a complementary male part. It is understood that these pair members may be reversed on either or both sides of the central member 42*j* without affecting the overall structure or assembly of the resulting modular body 12.

Figure 7:
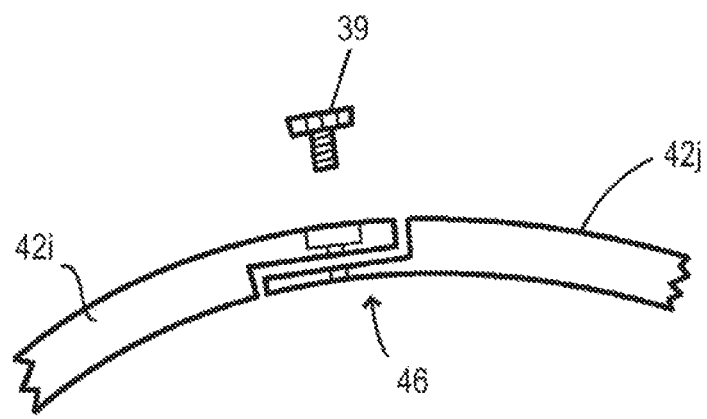
FIG. 7 is a schematic of another connector system that may be used with the various elements of a modular collar body.
Figure 8:
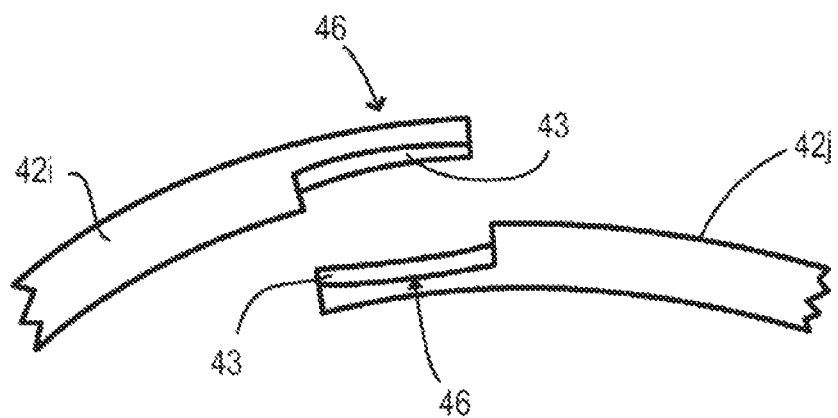
FIG. 8 is a schematic of a magnetic connector system that may be used with the various elements of a modular collar body.

FIG. 7 illustrates an alternate fastening mechanism suitable for use in these embodiments. In this embodiment each of the central member 42*j* and the individual side members 42*i* and 42*k* contain a complimentary notch that engages with the other to form a unitary structure. The notches may be held in place using a fastener 39 such as a screw, clip, or pin. FIG. 8 illustrates an alternate configuration of this mating system in which the central member 42*j* is fastened to the side members 42*i* and 42*k* using magnetic connectors 43 and 46 having an opposite polarity.

Figure 9:
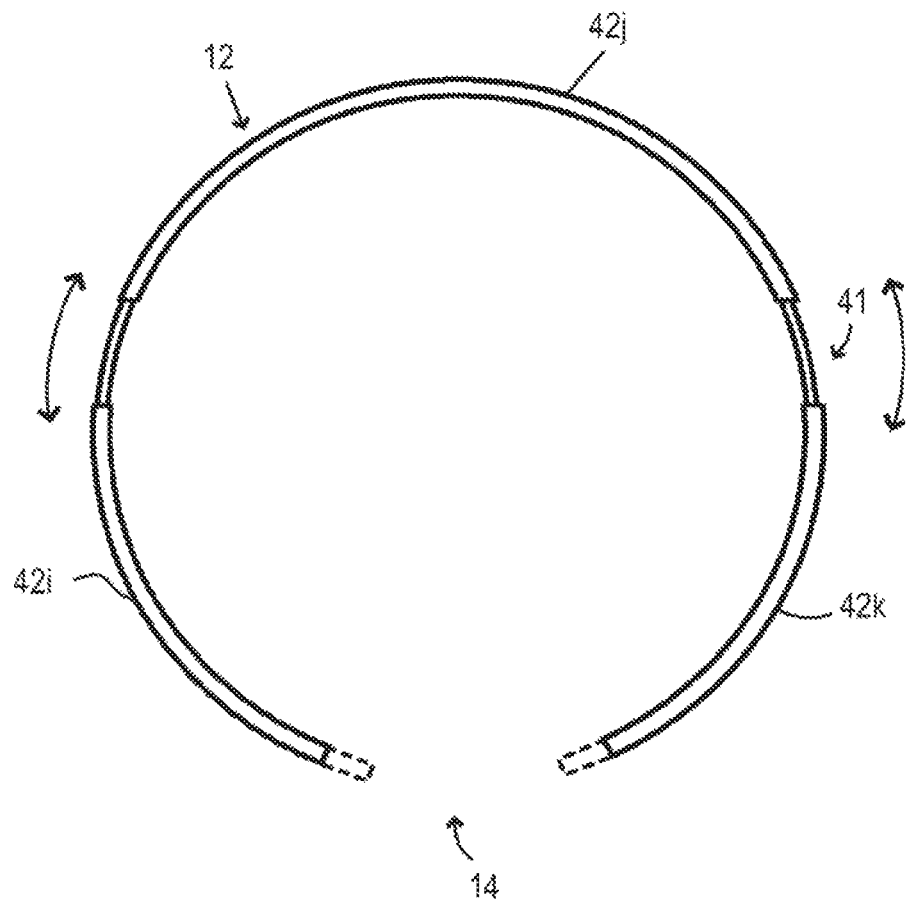
FIG. 9 is a schematic of an expandable collar body.
Figures 10, 11:
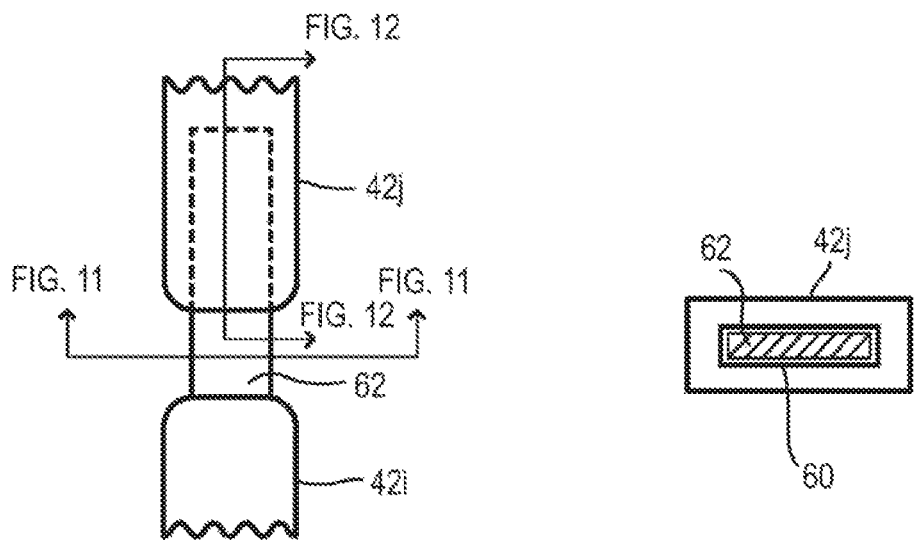
FIG. 10 is a schematic of connectors that may be used with the various elements of an expandable collar body.
FIG. 11 is a cross-sectional view through the connector system illustrated in FIG. 10.
Figure 12:
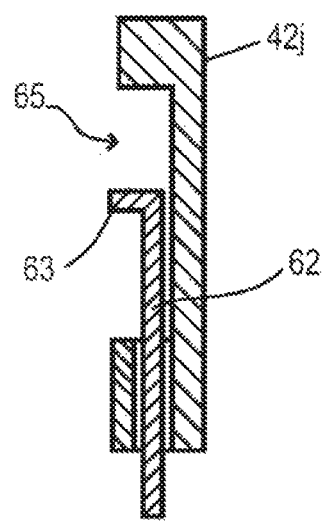
FIG. 12 is another cross-sectional view through the connector system illustrated in FIG. 10.
Figure 13:
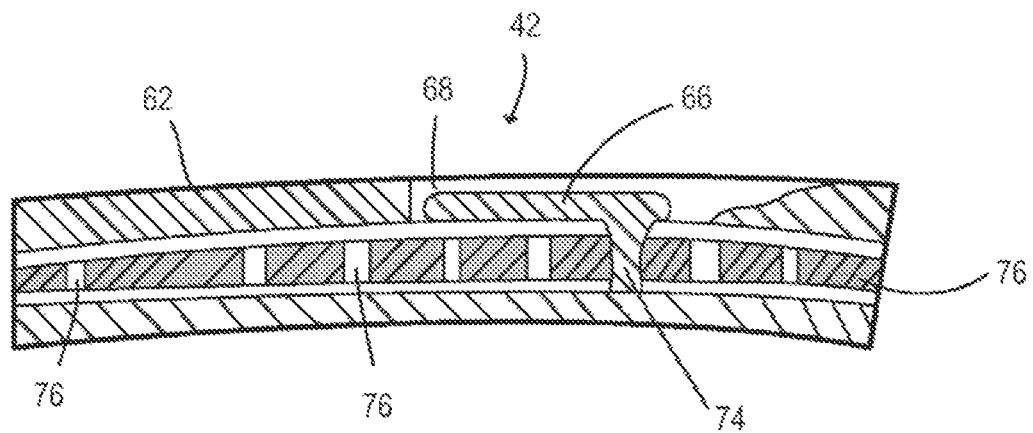
FIG. 13 is a schematic of a detents-and-notches size adjustment system.

In some embodiments, the adjustable collar body 12 is provided as a unitary device in which the side members 42*i* and 42*k* are slidably engaged with the central member 42*j*. FIG. 9 illustrates such an adjustable collar body 12 in which the side members 42*i* and 42*k* are disposed in a forward position relative to the central member 42*j*, thereby increasing the diameter D of the collar body 12. FIGS. 10-12 illustrate one slidable engagement mechanism in which central member 42*j* provides a channel 60 and receiver slot 65 into which sliding tab 62 from the side member engages. Sliding tab 62 comprises stopper 63 that prevents disengagement of side member from central member 42*j* and limits the maximum extension of that side member. The side members may be held in a fixed position relative to the central member 42*j* by any convenient mechanism. For example, the sides may be held in place by a simple frictional engagement between the channel 60 and the tab 62. Alternatively, as illustrated in FIG. 13, the side members may be secured by detents 74 and a series of notches 76. FIG. 13 illustrates a configuration in which notches 76 are present on sliding tab 62 which engage with a single detent 74 on central member 42*j*. Detent 74 extends from side member 66 that is attached to central member 42*j* at pivot 68. Side member 66 may be accessible to the user when the collar 10 is not worn in order to manually release detent 74 from notch 76. In one embodiment, detent 74 may allow unidirectional movement from notch to notch in order to facilitate proper fit after collar 10 is donned. In this embodiment, detent 74 may be used as the stopper by fashioning a notch 76 in a manner that prevents further extension of the side member. It is understood that this system of detents and notches may be reversed such that the detent(s) is/are present on the side member and the notches present on the central member 42*j*. Other fasting mechanisms are known to those of skill in the art including, for example a friction or thumbwheel screw that can either engage with a receiver or merely act to clamp together the individual components.

Adjustable Compressors

Figure 14:
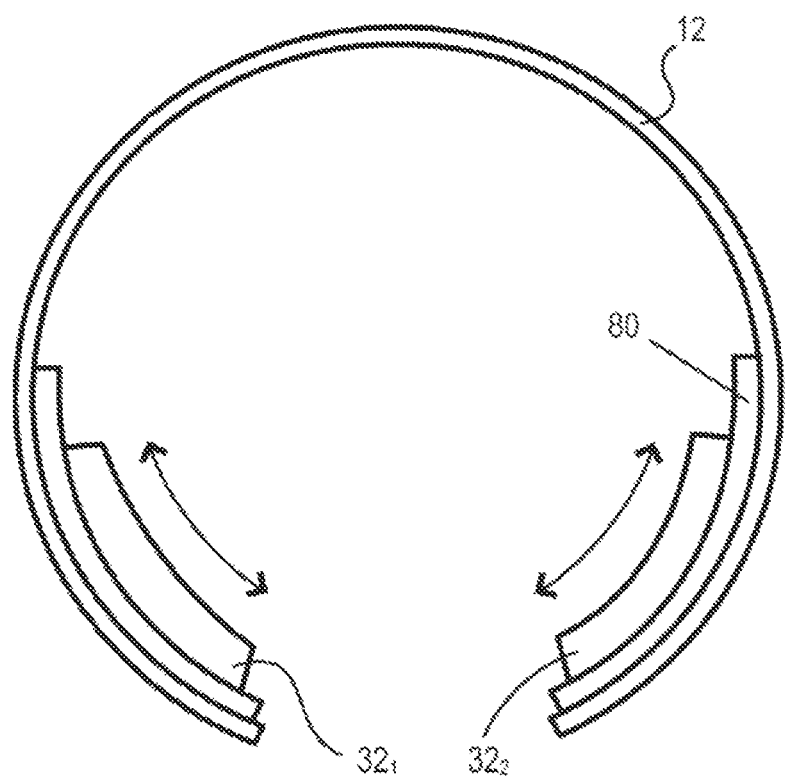
FIG. 14 is a schematic of a collar body having adjustable compressors.
Figure 15:
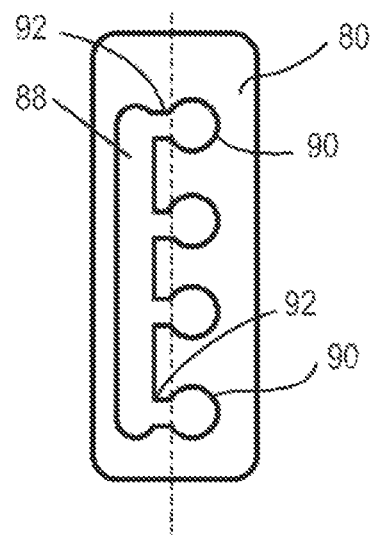
FIG. 15 is a schematic of a collar body mating system for use with adjustable compressors.
Figure 16:
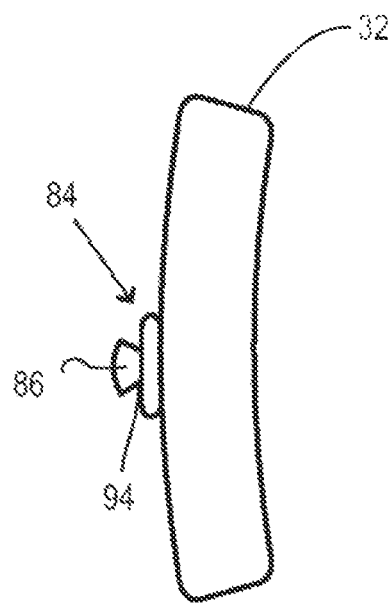
FIG. 16 is a schematic of an adjustable compressor and engagement mechanism.

In some embodiments, the invention also provides collars 10 that have adjustable compressors 32 on the collar 10 or the collar body 12. FIG. 14 illustrates one embodiment in which compressors $32_1$ and $32_2$ are slidably engaged with body 12 such that the compressors may be disposed at a plurality of locations along the inner surface of the collar 10 and/or body 12 in a direction substantially parallel to the longitudinal axis. In some embodiments, compressors 32 are slidably engaged on a slide rail 80. FIGS. 15 and 16 illustrate one example of an engagement mechanism between the slidable compressors 32 and the collar body 12. FIG. 15 illustrates a slide rail 80 that may be mounted along the longitudinal axis of collar body 12. Slide rail 80 has a longitudinal slot 88 and a plurality of openings 90 that are contiguous with slot 88. Optionally, each opening 90 is defined by a reduced-size neck 92 and a body portion. Each opening 90 corresponds to a discrete position that can accept compressor 32 and is capable of securely fixing compressor 32 to collar body 12.

FIG. 16 illustrates compressor 32 that may be engaged with slide rail 80 illustrated in FIG. 15. Compressor 32 comprises a slidable engagement member 84 on its outward facing side. Engagement member 84 has a head portion 86 and a neck portion 94 that has a larger diameter than neck portion 94.

Figure 17:
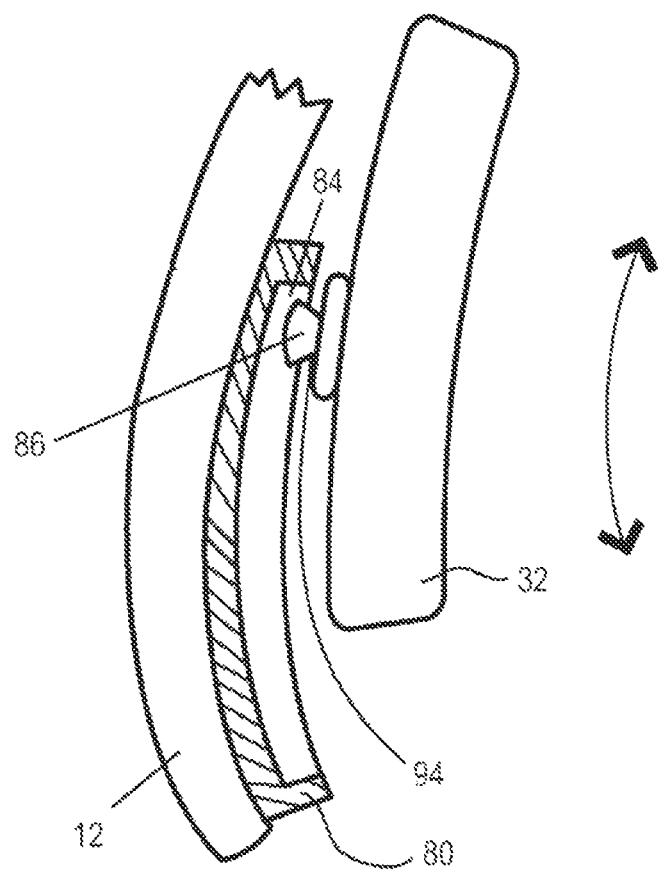
FIG. 17 is a schematic showing an adjustable compressor engaged with a collar body.

FIG. 17 illustrates a cross-sectional view of engagement member 84 engaged with slide rail 80. Specifically, neck portion 94 is adapted to slide freely along slot 88 and through neck 92 to engage head portion 86 within the body portion of opening 90, thereby locking compressor 32 into place. In one embodiment, engagement member 84 comprises an elastomeric material (e.g., rubber). The use of an elastomeric material for the sliding member 84 may allow the sliding member 84 to be easily secured to the openings 90, and provide resiliency such that purposeful amount of effort is required to disengage the sliding member 84. The sliding member 84 may be made of any other suitable material in other embodiments.

Figure 18:
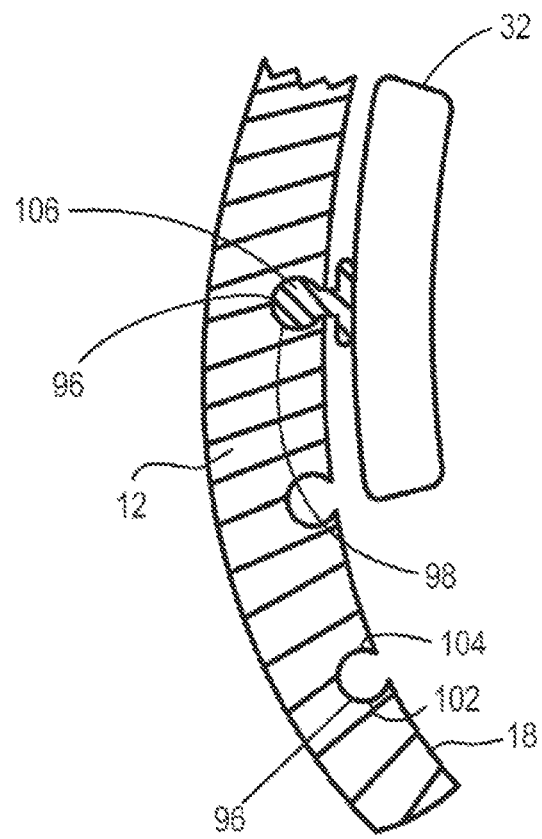
FIG. 18 is a schematic showing another adjustable compressor engaged with a collar body.

FIG. 18 illustrates an alternate engagement mechanism for adjustable compressors 32. In this embodiment, compressor 32 has a connector 98 on its outward-facing surface. Connector 98 may be configured to have, for example, a neck portion and a larger head portion 106. Body 12 is contains a plurality of cavities 96 configured to receive head portion 106. Cavities 96 may have a keyhole configuration with an enlarged portion 102, adapted to receive head portion 106, and a narrow portion 104, or neck, adapted to receive the neck portion of connector 98. In some embodiments, the portion of body 12 containing cavities 96 is constructed of sufficiently resilient material (e.g., an elastomeric material) to yield in order to accept head portion 106 under the application of a perpendicular force, hold connector 98 relatively immobile once in place, and resist releasing connector 98 under a lateral force (i.e., approximately parallel to the longitudinal axis of collar 10). Optionally, the collar system provides a plurality of matched compressor 32 pairs having different thicknesses (heights) and/or shapes. The user can select a compressor 32 pair having the appropriate thickness and/or shape in order to customize and optimize fit and neck vein pressure.

Figure 19:
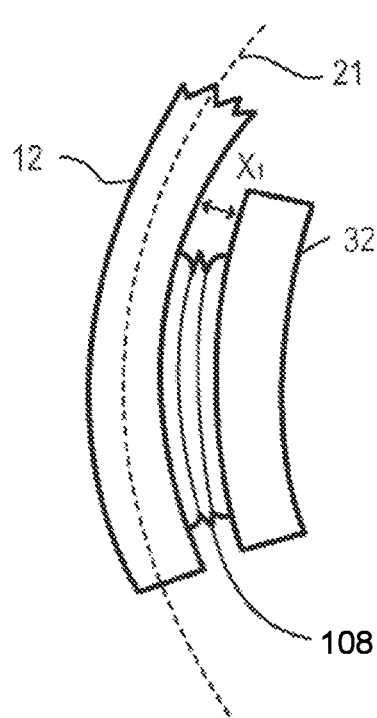
FIG. 19 is a schematic showing an expandable compressor in a compressed state.
Figure 20:
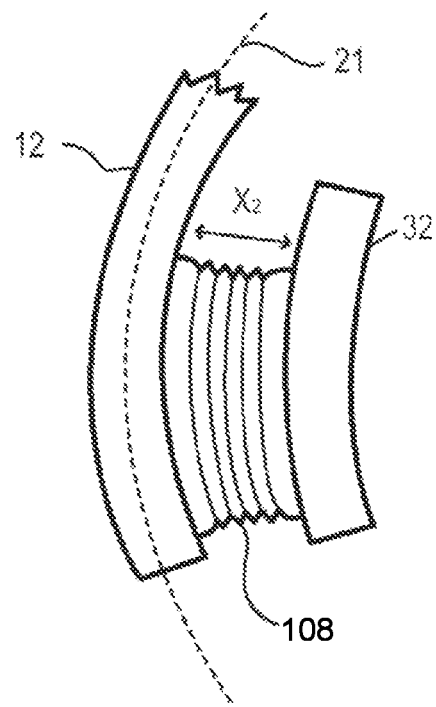
FIG. 20 is a schematic showing an expandable compressor in an expanded state.

In other embodiments, the invention provides a collar 10 and/or collar body 12 having compressors 32 that are adjustable in a direction perpendicular to the longitudinal axis of the collar. This form of adjustment allows the user to vary the amount of neck vein pressure applied by compressors 32. FIGS. 19-20 illustrate one embodiment in which compressor 32 is mounted on an expandable element 108 that is attached to body 12. Expandable element 108 is adapted to reversibly adjust the height of compressor 32 from height X1 (FIG. 19) to height X2 (FIG. 20). In some embodiments, the compressor 32 height may be regulated by a mechanical scissor lift positioned between the compressor body 32 and the collar body 12. The scissor lift may be a friction joint that requires the application of more force to open/close (extend/retract) than the desired force to be applied against the neck. Modulation of the force requirement to operate the scissor lift also may serve as a pressure limiter such that the scissor lift retracts under a force that would apply excessive neck vein pressure. In other embodiments, the compressor 32 height may be controlled by an inflatable element placed between the compressor body 32 and the collar body 12. Optionally, the inflatable element also contains a pressure release valve which may be set to release the inflation gas at pressures that would apply excessive neck vein pressure to the subject.

In other embodiments, the compressor height may be adjusted using a screw mechanism. For example, the compressor may have a threaded screw or rod extending from the outward-facing surface and the one or more cavities 96 may be threaded to accept the compressor screw. For adjustment, the appropriate cavity 96 is selected to position the compressor 32 in the correct longitudinal position along the longitudinal axis of body 12. Compressor height is then adjusted by the depth to which the compressor is screwed into selected cavity 96.

In other embodiments, the compressor height may be passively adjusted by placing a spring between the compressor 32 and body 12. The neck vein pressure may be controlled by selection of a spring with the appropriate compressive resiliency.

Collar with Fit Adjuster

Figure 21:
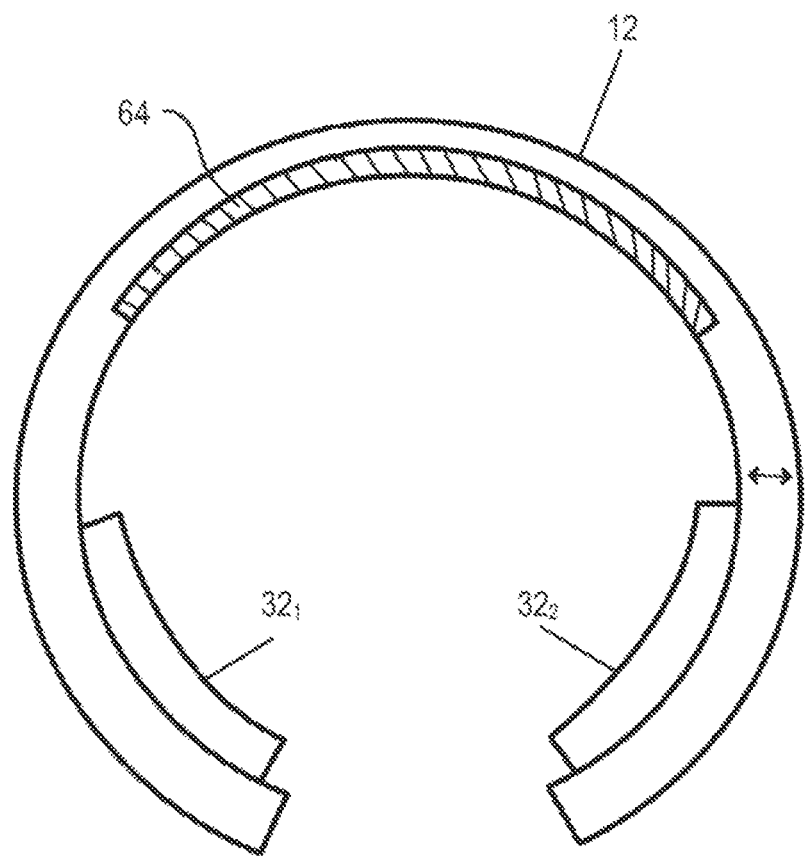
FIG. 21 is a schematic of a unitary collar body with a fit adjustment element on the body-facing surface.

The invention also provides collars having a fit adjustment element that may be used with modular and adjustable collars or unitary collars. FIG. 21 illustrates a unitary collar body 12 having a fit adjustment element 64 disposed on the body-facing surface. Optionally, the fit adjustment element 64 is positioned toward the back (dorsal) region of body 12. The purpose of the fit adjustment element 64 is to improve collar 10 fit on differently-sized necks. For example, a collar 10 may be fitted to a user such that compressors 32 are well-positioned to contact and apply pressure to the neck veins but the collar may be a fractional size too large, thereby leaving a gap between the back of the neck and the collar. The fit adjustment element 64 may be used to fill this gap and/or generally provide a more secure fit for the collar when worn around the neck. In another embodiment, the invention provides a modular collar body 12 having a fit adjustment element 64 on the central member 42j.

In one embodiment, the fit adjustment element 64 is removable. Optionally, the invention provides a system having a plurality of fit adjustment elements 64 of different sizes such that the user can select the most appropriate size to maximize comfort, fit, and proper positioning of the compressors. In another embodiment, the fit adjustment element 64 is inflatable.

Bend Angle Measuring System

Figure 22:
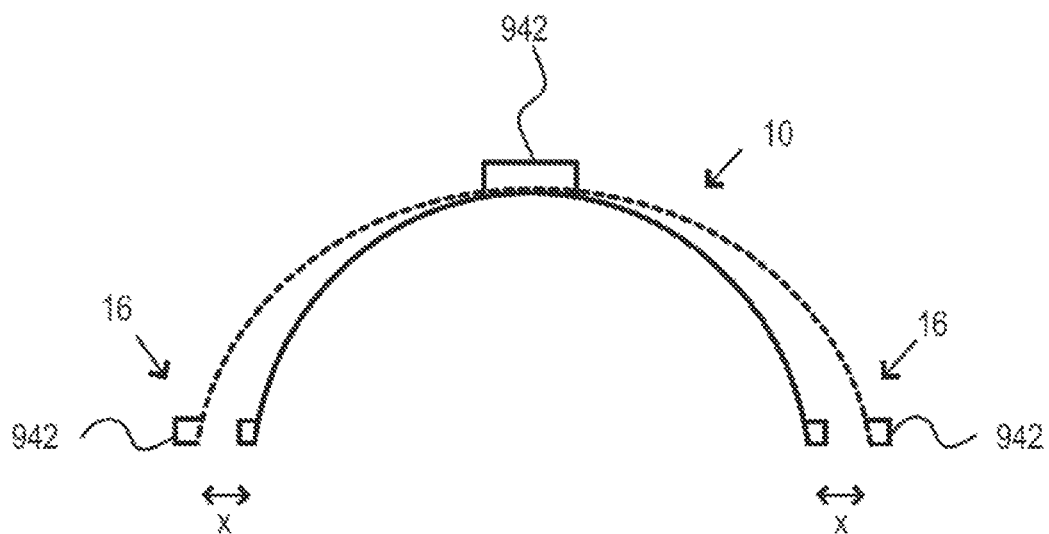
FIG. 22 is a schematic showing a collar with a plurality of bend angle sensors.

The invention also provides systems and methods for measuring or inferring the amount of pressure applied by collar 10 to the neck veins using a bend angle measuring system. As described above, collar 10, including body 12, is constructed to have an inwardly directed bias when the collar 10 is worn such that compressors 32 apply pressure to the neck veins. The pressure applied by compressors 32 can be measured for any particular value of opening 14 and is a function of the specific materials and construction of collar 10. For any collar 10, the amount of pressure applied by compressors also is a function of the bend angle of collar 10 when it is worn. Thus, the compressor pressure can be inferred from the bend angle of the collar at various locations. Accordingly, the invention provides a unitary or modular collar 10 having one or more bend angle sensors. FIG. 22 illustrates a collar 10 having a bend angle sensor 942 positioned on the outwardly-facing side of collar 10, in the middle of the longitudinal collar axis that normally would be positioned directly over the wearer's spine. Optionally, and as illustrated in FIG. 22, collar 10 further comprises a bend angle sensor 942 at each of the end portions 16. For embodiments in which only a single centrally-located bend angle sensor is present, the compressor pressure may be calculated from the bend angle made by the collar in that region. For embodiments in which a plurality (e.g., two or three) bend angle sensor are present, the compressor pressure may be calculated as a function of all measured bend angles. Optionally, collar 10 further comprises a microprocessor and digital memory storage system to measure and record the bend angles and/or compressor pressures. These data may be transmitted in delayed or real-time by an optional radio transmitter. FIG. 22 also illustrates the configuration of collar 10 in its resting configuration (solid line) and a stretched configuration as it may be when worn (dashed line), wherein the end portions 16 are outwardly deflected by a distance "x".

Figure 23:
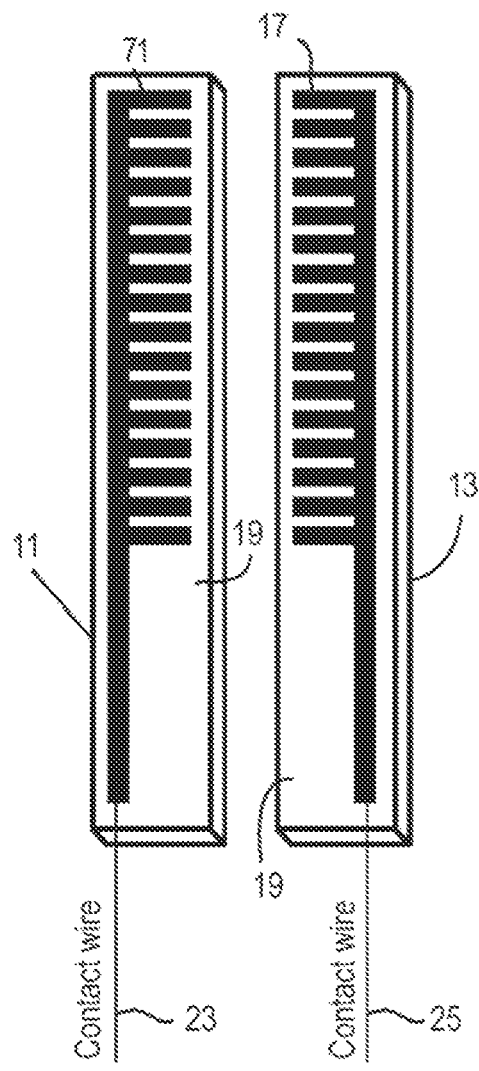
FIG. 23 is a schematic illustrating the components of one type of bend angle sensor.
Figure 24:
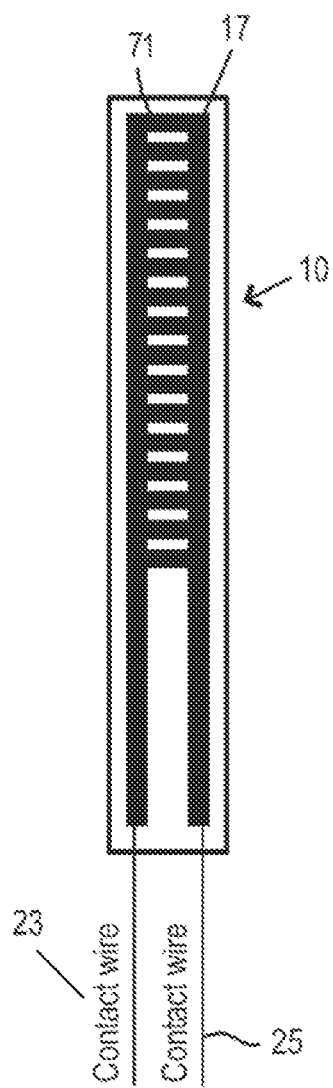
FIG. 24 is a schematic of an assembled bend angle sensor.
Figure 25:
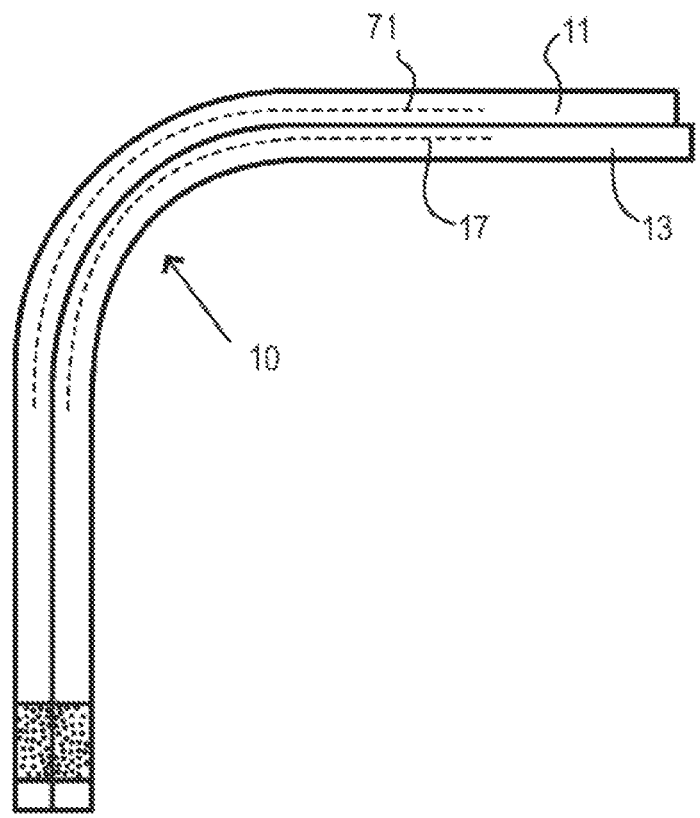
FIG. 25 is a schematic of a bend angle sensor within a protective housing.

A variety of suitable bend angle sensors are known in the art. For example, FIG. 23 is a schematic of a capacitive bend angle sensor such as those described in U.S. Pat. No. 5,610,528. The capacitive sensors include at least two elements 11, 13 that consist of a flexible, electrically insulating material such as plastic. One surface of each element has a comb pattern 71, 17 of conducting material, such as a metal film or conducting polymer, and a dielectric layer, 21 covering the comb material. FIG. 24 illustrates the assembled bend angle sensor in which the two elements 11,13 are placed together such that the two comb patterns 71,17 are in close proximity, separated only by one or more dielectric layers. The two elements 11, 13 are then bonded together. Preferably, the comb patterns 71, 17 of each of the elements 11, 13 are disposed near one end of the elements, and the elements are bonded together on the opposite end as shown in FIG. 25. Electrical contacts 23, 25 (wires) are affixed to the conducting comb patterns 71, 17. The two elements 11,13 may be placed in flexible plastic tubing (not shown) or other structure that contains and protects the two elements 11,13, and keeps them pressed together.

For purposes of clarity and conciseness of the description, not all of the numerous components shown in the schematic are described. The numerous components are shown in the drawings to provide a person of ordinary skill in the art a thorough enabling disclosure of the present invention. The operation of many of the components would be understood to one skilled in the art.

Each of the additional features and teachings disclosed herein can be utilized separately or in conjunction with other features and teachings to provide the present invention. Representative examples utilizing many of these additional features and teachings, both separately and in combination, are described in further detail with reference to the attached drawings. This detailed description is merely intended to teach a person of skill in the art further details for practicing preferred aspects of the present teachings and is not intended to limit the scope of the claims. Therefore, combinations of features disclosed in the detailed description may not be necessary to practice the teachings in the broadest sense and are instead taught merely to describe particularly representative examples of the present teachings.

Moreover, the various features of the representative examples and the dependent claims may be combined in ways that are not specifically and explicitly enumerated in order to provide additional useful embodiments of the present teachings. In addition, all features disclosed in the description and/or the claims are intended to be disclosed separately and independently from each other for the purpose of original disclosure, as well as for the purpose of restricting the claimed subject matter independent of the compositions of the features in the embodiments and/or the claims. All value ranges or indications of groups of entities disclose every possible intermediate value or intermediate entity for the purpose of original disclosure, as well as for the purpose of restricting the claimed subject matter. The dimensions and the shapes of the components shown in the figures are designed to help understand how the present teachings are practiced but are not intended to limit the dimensions and the shapes shown in the examples.

What is claimed is:

1. A modular collar system for constructing a collar sized to be worn around the neck of a human subject, the system comprising:

a central member having a first mating pair member at a first end and a second mating pair member at a second end;

a first side member having a complimentary first mating pair member at a first end and a first compressor at a second end; and a second side member having a complimentary second mating pair member at a first end and a second compressor at a second end;

wherein a collar defining an arc of greater than 180° is formed by mating the first mating pair member of the central member with the complimentary first mating pair member of the first side member and mating the second mating pair member of the central member with the complimentary second mating pair member of the second side member, wherein the second end of the first side member and the second end of the second side member are free ends having a gap therebetween such that the constructed collar does not extend around an entirety of the circumference of the neck, wherein the first and second compressors are positioned on the collar to contact two or more neck veins of the human subject when the collar is worn around the neck, wherein the collar is adapted to exert an inwardly-directed force on the first and second compressors when worn, and wherein the first and second compressors are slidably engaged with the first and second side members, respectively.

2. The system of claim 1, wherein the first mating pair member and the complimentary first mating pair member form a reversible attachment and/or the second mating pair member and the complimentary second mating pair member form a reversible attachment.

3. The system of claim 1, wherein the first and second compressors are expandable in a direction facing the neck when worn.

4. The system of claim 1, wherein the central member further comprises a fit adjustment element attached to a surface facing the neck when worn.

5. The system of claim 4, wherein the fit adjustment element is inflatable.

6. The system of claim 1, wherein the system comprises two or more central members.

7. The system of claim 1, wherein the first and second compressors are reversibly attachable to the first and second side members, respectively.

8. The system of claim 1, further comprising a bend angle sensor configured and positioned to detect a bend angle of the collar.

9. An expandable collar sized to be worn around the neck of a human subject, the collar comprising:

a central member having a first end and a second end;

a first side member having a first end slidably engaged with the first end of the central member and a second end comprising a first compressor; and a second side member having a first end slidably engaged with the second end of the central member and a second end comprising a second compressor;

wherein the central, first side, and second side members define an arc of less than 360° and greater than 180° having a diameter;

wherein the second end of the first side member and the second end of the second side member are free ends having a gap therebetween such that the constructed collar does not extend around an entirety of the circumference of the neck;

wherein the diameter is altered by the slidable engagement of the first side member and the central member and/or by the slidable engagement of the second side member and the central member; and wherein the collar is adapted to exert an inwardly-directed force on the first and second compressors when worn.

10. The expandable collar of claim 9, wherein the first and second compressors are slidably engaged with the first and second side members, respectively.

11. The expandable collar of claim 9, wherein the first and second compressors are removably attached to the first and second side members, respectively.

12. The expandable collar of claim 9, wherein the first and second compressors are expandable in the a direction facing the neck when worn.

13. The expandable collar of claim 9, wherein the central member further comprises a fit adjustment element attached to a surface facing the neck when worn.

14. The modular collar of claim 13, wherein the fit adjustment element is inflatable.

15. The expandable collar of claim 9, further comprising a bend angle sensor configured and positioned to detect a bend angle of the collar.

16. A collar sized to be worn around the neck of a human subject, the collar comprising:

a central member having a first end and a second end;

a first side member having a first end engaged with the first end of the central member and a second end comprising a first compressor; and a second side member having a first end engaged with the second end of the central member and a second end comprising a second compressor;

wherein the central, first side, and second side members define an arc of less than 360° and greater than 180° having a diameter that is alterable;

wherein the second end of the first side member and the second end of the second side member are free ends having a gap therebetween such that the constructed collar does not extend around an entirety of the circumference of the neck;

wherein the first and second compressors are movably engaged with the first and second side members, respectively; and wherein the collar is adapted to exert an inwardly-directed force on the first and second compressors when worn.

17. The collar of claim 16, wherein the first and second compressors are slidably engaged with the first and second side members, respectively.

18. The collar of claim 16, wherein the first end of the first side member has a first releasable engagement with the first end of the central member and the first end of the second side member has a second releasable engagement with the second end of the central member, and wherein the diameter is alterable by replacing one or more of the first side member, the second side member, and the central member at the first or second releasable engagements.

19. The collar of claim 16, wherein the first end of the first side member has a first slidable engagement with the first end of the central member, and wherein the diameter is altered by the first slidable engagement of the first side member and the central member.

20. The collar of claim 19, wherein the first end of the second side member has a second slidable engagement with the first end of the central member, and wherein the diameter is altered by the second slidable engagement of the second side member and the central member.

21. The collar of claim 16, wherein the first end of the second side member has a second slidable engagement with the first end of the central member, and wherein the diameter is altered by the second slidable engagement of the second side member and the central member.

22. The collar of claim 16, further comprising a bend angle sensor configured and positioned to detect a bend angle of the collar.

* * * * *